US007182748B1

(12) United States Patent
Potter et al.

(10) Patent No.: US 7,182,748 B1
(45) Date of Patent: Feb. 27, 2007

(54) SYRINGE AND CAPSULE THEREFOR

(75) Inventors: Charles Potter, Standlake (GB); David Stuart Potter, Cowes (GB); Brian Bellhouse, Islip (GB); John Christopher Greenford, Abingdon (GB); Fiona Carter, Oxford (GB); Stuart Graham Weekes, Iffley (GB); Colin Sheldrake, Henley on Thames (GB)

(73) Assignee: PowderJect Research Limited, Oxford (GB)

( * ) Notice: Subject to any disclaimer, the term of this patent is extended or adjusted under 35 U.S.C. 154(b) by 0 days.

(21) Appl. No.: 09/462,218

(22) PCT Filed: Jul. 6, 1998

(86) PCT No.: PCT/GB98/01980

§ 371 (c)(1),
(2), (4) Date: May 22, 2000

(87) PCT Pub. No.: WO99/01169

PCT Pub. Date: Jan. 14, 1999

(30) Foreign Application Priority Data

Jul. 4, 1997 (EP) .................................. 97304909

(51) Int. Cl.
*A61M 5/30* (2006.01)

(52) U.S. Cl. ............................ 604/70; 604/68; 604/85

(58) Field of Classification Search .................. 604/57, 604/58, 68, 69, 70, 82, 84, 85, 87, 89, 90, 604/91, 200, 202, 204, 226
See application file for complete search history.

(56) References Cited

U.S. PATENT DOCUMENTS 2,636,493 A * 4/1953 Lockhart ..................... 604/90
2,699,166 A * 1/1955 Dickinson, Jr. et al. ...... 604/70
5,125,892 A 6/1992 Drudik
5,614,217 A 3/1997 Chiprich et al.
5,630,796 A 5/1997 Bellhouse et al.
6,004,286 A 12/1999 Bellhouse et al.
6,010,478 A * 1/2000 Bellhouse et al. ............ 604/70
6,013,050 A 1/2000 Bellhouse et al.

FOREIGN PATENT DOCUMENTS

DE 2118993 11/1972
EP 0144551 A1 6/1985
WO WO 94/24263 10/1994

(Continued)

*Primary Examiner*—Kevin C. Sirmons
*Assistant Examiner*—Laura C. Schell
(74) *Attorney, Agent, or Firm*—Foley & Lardner LLP

(57) ABSTRACT

A syringe, for use in the delivery of a dose of a therapeutic agent entrained within a pressurized fluid flow, includes an upstream portion, an intermediate portion, a downstream portion, and an actuator mechanism for initiating a flow of the fluid through the syringe. The upstream portion is interfaced with a source of fluid under pressure. The intermediate portion, which is interposed between the upstream and downstream portions, includes first and second members that are coupled together to provide a closed pocket for containing the dose. One of the first and second members is moveable relative to the other within the syringe to provide an open configuration in which the pocket is opened to expose the dose for entrainment by the fluid as it flows through the intermediate portion and to and through the nozzle. Also provided is a capsule formed from the first and second members.

34 Claims, 7 Drawing Sheets

FOREIGN PATENT DOCUMENTS

| | | |
|---|---|---|
| WO | WO 96/04947 | 2/1996 |
| WO | WO 96/12513 | 5/1996 |
| WO | WO 96/25190 | 8/1996 |
| WO | WO 97/34652 | 9/1997 |
| WO | WO 99/01168 | 1/1999 |

* cited by examiner

SYRINGE AND CAPSULE THEREFOR

This application is a 371 of International Patent Application Number PCT/GB98/01980, filed Jul. 6, 1998, designating the United States, from which priority is claimed pursuant to 35 U.S.C. §365(c) and which is incorporated herein by reference.

TECHNICAL FIELD

The present invention relates generally to a syringe for use in the delivery of a dose of a therapeutic agent entrained within a pressurized fluid flow. More particularly, the invention is drawn to a capsule for containing a dose of a therapeutic agent to be delivered within a fluid flow, and to syringes which comprise such capsules.

BACKGROUND OF THE INVENTION

A number of needleless syringes are disclosed, for example, in International Patent Applications WO 94/24263 and WO 96/25190. These syringes are commonly used for delivery of therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection), as well as for prophylactic, diagnostic or other medical treatments. These syringes generally have an upstream portion, which contains, or is arranged to be connected to, a source of fluid under pressure, a downstream nozzle portion, and, between the upstream and downstream portions, an intermediate portion which accommodates a dose of a therapeutic agent to be delivered, and an actuator mechanism for initiating a flow of the fluid from the source so that the dose is entrained in the fluid flow through the intermediate portion and hence to and through the nozzle for delivery to a target site.

In these syringes, the therapeutic agent is provided in a sealed capsule having upstream and downstream rupturable diaphragms. The diaphragms are sealed together about their edges and contain in the chamber formed therebetween a dose of the agent which is to be delivered. Upon release of a compressed gas, the gas pressure quickly builds up behind the capsule until the differential pressure across the capsule becomes sufficient to burst the capsule diaphragms, thus releasing through the spent capsule and nozzle a gas flow in which the therapeutic agent is entrained.

Although this arrangement has proved to be very successful, it would be desirable to provide a capsule which is cheap to manufacture, from which the full dose of drug will reliably be flushed out and entrained in the gas stream, and which is sufficiently robust to avoid the production of debris.

SUMMARY OF THE INVENTION

A capsule is provided for use in a syringe for delivering a therapeutic agent. The capsule is adapted for containing a dose of the therapeutic agent which is to be delivered from the syringe within a pressurized fluid flow. The capsule comprises a first member and a second member which are coupled together to provide a closed pocket for containing the dose. One of the members is moveable relative to the other member when a portion of the capsule is contacted with a pressurized fluid flow, such that a passage is formed through the capsule, and the pocket is opened to expose the dose for entrainment within fluid flowing through the newly opened passage. The first and second members can be coupled together to form the closed pocket by a resilient coupling means which resists initial movement of the members relative to each other. Further, the capsule can be provided such that the closed pocket is prefilled with the dose of the therapeutic agent, and the first and second members and coupled together in a sealed configuration.

The first member of the capsule can be configured as a plug which fits within the second member of the capsule which is configured as a housing for the plug. The pocket, which contains the dose of the therapeutic agent, can be provided by a space established between the outer surface of the plug and the inner surface of the housing where these two elements do not contact each other. Preferably, a cavity or recess provided in the plug and/or housing is used to establish the pocket. In any event, the capsule can be constructed such that the pocket provides a volumetric space for containing a known amount of the therapeutic agent.

Alternatively, the first and second members can be first and second halves of a vertically divided plug. In this example, the first and second halves of the plug contact each other at opposing faces thereof, and the closed pocket is provided by corresponding cavities which are disposed within the opposing faces.

In another aspect of the invention, a syringe is provided for delivering a dose of a therapeutic agent within a pressurized fluid flow. The syringe comprises, in operative combination, an upstream portion which is interfaced with a source of fluid under pressure; a downstream nozzle portion; an intermediate portion arranged between the upstream and downstream portions; and an actuator mechanism for initiating a flow of fluid from the source of fluid to the intermediate portion. The intermediate portion comprises first and second members which are coupled together to provide a closed pocket for containing the dose of the therapeutic agent. As with the capsule of the present invention, one of the first and second members is moveable within the syringe relative to the other member. Accordingly, pressure exerted by the fluid causes one of the members to move relative to the other member such that a passage is formed through the intermediate portion, and the pocket is opened to expose the dose for entrainment in fluid flowing through the passage and into the downstream nozzle portion.

The first member of the intermediate portion of the syringe can be configured as a tubular housing which has an upstream opening and a downstream opening, and the second member of the intermediate portion can be configured as a plunger having a lower end which is disposed within and closes off the downstream opening of the tubular housing. Here, the closed pocket is provided by a space established between the lower end of the plunger and the inner surface of the downstream opening. An upper end of the plunger extends toward the upstream portion of the syringe and is supported by a bar which is supported at both ends by the intermediate portion of the syringe and is initially deflected towards the upstream portion of the syringe.

In use, pressure exerted by the fluid causes the bar to travel through a dead-center position and deflect towards the downstream portion of the syringe, thereby causing the lower end of the plunger to dislodge from the downstream opening and move in a downstream direction relative to the housing to both open the closed pocket and provide a passage through the intermediate portion of the syringe. If desired, the intermediate portion of the syringe can further include means for providing resistance against initial movement of the first or second member relative to the other member, thereby holding the dose of the therapeutic agent within the closed pocket until desired delivery conditions (e.g., sufficient pressure) are established within the syringe.

Also provided is a syringe for delivering a dose of a therapeutic agent within a pressurized fluid flow. The syringe comprises any one of the capsules of the present invention disposed within an intermediate part of the syringe.

Additional objects, advantages and novel features of the invention will be set forth in part in the description which follows, and in part will become apparent to those skilled in the art upon examination of the following, or may be learned by practice of the invention.

BRIEF DESCRIPTION OF THE FIGURES

Some examples of syringes and capsules constructed in accordance with the present invention are illustrated in the accompanying drawings in which.

DETAILED DESCRIPTION OF THE PREFERRED EMBODIMENTS

Figure 1:
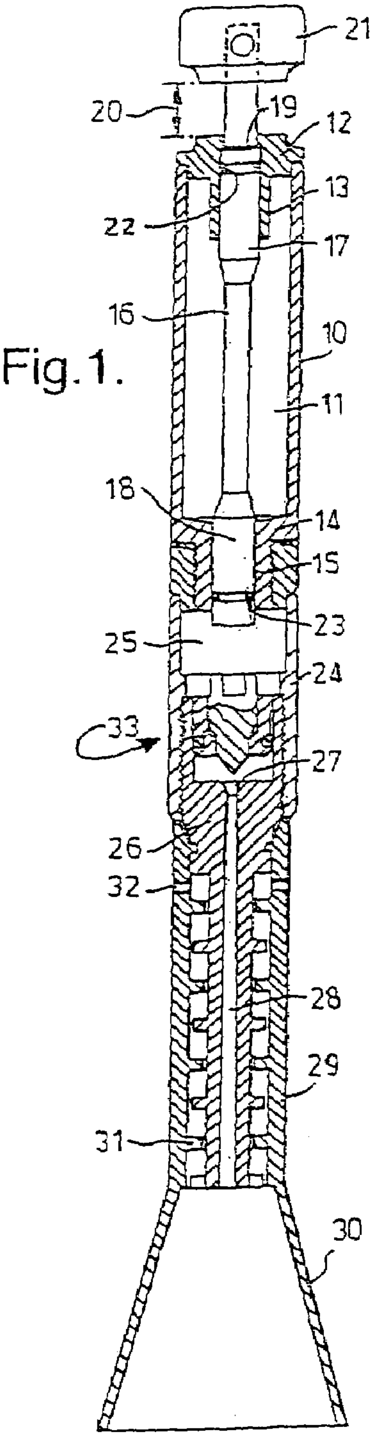
FIG. 1 is an axial section through a first example of a syringe.

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a fluid" or "a gas" includes mixtures of two or more such fluids or gases, and the like.

A. Definitions

Unless defined otherwise, all technical and scientific terms used herein have the same meaning as commonly understood by one of ordinary skill in the art to which the invention pertains. The following terms are intended to be defined as indicated below.

As used herein, the term "therapeutic agent" intends any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), erodible polymers (such as polylactic acid, polyglycolic acid, and copolymers thereof), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and plastics, Danbury, Conn.), polyoxyethylene-sorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

B. General Methods

The present invention relates to novel capsules and/or syringe device configurations for containing a dose of a therapeutic agent which is to be delivered within a pressurized fluid flow. Thus, in accordance with the present invention, a syringe is provided which comprises an upstream portion which is interfaced with (i.e., contains, or is arranged to be connected to) a source of fluid under pressure, a downstream nozzle portion, and, arranged between the upstream and downstream portions, an intermediate portion which initially contains the dose of the therapeutic agent. The intermediate portion includes first and second members which are coupled together to form a closed pocket for containing the therapeutic agent. One of these members is moveable relative to the other. The syringe further includes an actuator mechanism for initiating a flow of the fluid from the source, whereupon pressure exerted by the fluid upon one or more components of the intermediate portion causes one of the first and second members to move relative to the other and thereby form a passage between, around, or through said members and open the pocket to expose the therapeutic agent for entrainment in the fluid as it flows through the intermediate portion and into and through the nozzle.

The first and second members may be formed or assembled integrally with the intermediate portion of the syringe, and the intermediate and downstream portions of the syringe may then be disposable. However, for ease of production, storage and distribution, particularly when the same basic syringe construction may be used for delivering a variety of different agents, the two members may be comprised of a capsule which, before use, is loaded into a chamber in the intermediate portion of the syringe.

A unique feature of the intermediate portion of the syringe and/or the capsule inserted therein is the provision of two operative components (the first and second members) which can be initially coupled together to provide a sealed container for the agent, and then opened under predictable conditions to allow delivery of the agent from the syringe.

The invention therefore also includes a capsule configured to contain a dose of a therapeutic agent and adapted to be accommodated within the chamber of a syringe between an upstream source of fluid under pressure and a downstream nozzle portion. The capsule thus comprises two members providing therebetween a closed pocket containing the agent, one of the members being adapted to move, when subjected to the fluid pressure, relative to the other member to open the pocket and expose the dose for entrainment in the fluid flowing through the chamber to the nozzle. For ease of handling, the capsule can be prefilled with the dose of the therapeutic agent, and then provided in a sealed condition ready for use within the syringe.

The two members of the syringe or capsule may be simple plastic moldings which have confronting surfaces which slide over each other. The surfaces may be coaxial cylindrical surfaces or other surfaces with confronting flat or curved planes parallel to the direction of movement. The pocket may then be provided by a recess or recesses, such as an annular groove, in one or both of the members, the pocket being closed on the upstream and downstream sides by the confronting surfaces. When the members move relative to one another, at least one surface rides off its confronting surface to open the pocket to the fluid flow, possibly between or around, but preferably through at least one of the members. The flow path itself may be opened upon the relative movement of the two members.

A resistance against the initial relative movement of the two members may be provided to ensure that the two members do not move relative to one another to release the dose prematurely, either before the fluid flow has reached substantially maximum velocity, or, in the case in which the flow path is opened by the relative movement of the members, before the pressure has built up sufficiently that when the flow path has been opened to release the fluid, it accelerates very quickly to maximum velocity. This resistance may take the form of an adequate interference fit (e.g., a frictional coupling) between the two members, or a complementary detent and/or projection which is overridden when the moveable member receives sufficient force from the fluid.

A close fit between the first and second members may be sufficient to seal the dose-containing pocket. However, seals such as O rings may be provided between the members. Also, when the capsule is a separate unit for insertion into a chamber of the syringe, an O ring or another seal may be provided between the capsule and syringe body to avoid fluid leakage past the capsule.

According to one preferred example, the first and second members (of either the intermediate portion of the syringe or of the capsule) are provided by a plug which is inserted into a housing. The plug and housing are moveable relative to each other, where either the plug moves relative to the housing within the syringe, or the housing moves relative to the plug within the syringe. The closed pocket which contains the dose of the therapeutic agent is provided by one or more spaces created between the plug and the housing. For example, the plug and housing can contact each other at upper and lower opposing faces such that a pocket is formed by an intermediate space established between the upper and lower opposing faces where the plug and housing do not contact each other.

Alternatively, the plug can have an enlarged head at a downstream side thereof, wherein the plug is retained within the housing by an interference fit between the enlarged head and the surrounding housing and an interference fit between the end opposite to the enlarged head and a different portion of the housing. In this case, the closed pocket is provided by the space between the inner surface of the housing and the outer surface of the plug (between the two areas of interference fit). Here, the plug is adapted such that, upon application of the fluid under pressure, the friction between the plug and capsule housing is overcome to force the plug towards the downstream portion of the syringe allowing the dose to escape from the pocket around the enlarged head. An optional stop can be provided which acts against a portion of the plug in order to prevent further movement of the plug through the capsule housing. For example, a simple structure can be provided if the end of the plug opposite to the enlarged head is provided with a second enlarged head of greater diameter than the enlarged head, so that abutment of the second enlarged head against a portion of the capsule housing provides the stop.

In another preferred example, the first and second members (of either the intermediate portion of the syringe or of the capsule) are respectively provided by first and second halves of a vertically divided plug. The first and second halves of the divided plug contact each other at their opposing faces, and the closed pocket is provided by corresponding cavities disposed within the opposing faces.

In still further examples, the first member of either the capsule or the intermediate portion of the syringe comprises a tubular housing having an upstream opening and a downstream opening. The second member comprises a plunger having a lower end which is disposed within and closes off the downstream opening of the housing. The closed pocket is provided by a space established between the lower end of the plunger and the inner surface of the downstream opening. The upper end of the plunger extends toward the upstream portion of the syringe and is supported by a central portion of a bar which is supported at both ends by the intermediate portion of the syringe and is initially deflected towards the upstream portion of the syringe. In use, the pressure exerted by the released pressurized fluid flow upon the intermediate portion of the syringe causes the bar to travel through a dead-center position and deflect towards the downstream portion of the syringe, thereby causing the lower end of the plunger to dislodge from the downstream opening of the housing (traveling in a downstream direction relative to the housing) to provide a passage through the intermediate portion of the syringe.

Alternatively, the first member of the capsule or intermediate portion of the syringe comprises a tubular housing having an upstream opening and a downstream opening. The second member comprises a disk having a centrally disposed plug attached thereto. The disk closes off the downstream opening of the tubular housing, and the plug extends toward the upstream portion of the syringe and closes off the upstream opening of the housing. The closed pocket is provided by an annular space established between the disk, the outer surface of the plug, and the inner surface of the housing. In operation, pressure exerted by the released fluid causes the plug to dislodge from the upstream opening and move in a downstream direction relative to the housing, thereby exerting sufficient pressure upon the disk to deform it and cause it to pass through the downstream opening and create a passage through the intermediate portion of the syringe.

Although the invention is applicable to syringes in which the dose is of any appropriate liquid or solid form or entrainment, and the fluid is a liquid or a gas, the invention is particularly applicable to needleless syringes in which the fluid is a compressible gas, such as helium, and the dose of the therapeutic agent is in particulate form, such as heavy microparticles coated with therapeutic agents, or powdered therapeutic agents for firing (e.g., transdermally) into tissue.

Referring now to the figures, a first example of a syringe of the present invention is illustrated in FIG. 1. The device of FIG. 1 is, except for the intermediate portion beat shown in FIGS. 2 and 3, substantially identical to that of FIGS. 1–3 of International Publication No. WO 94/24263.

Thus, the syringe comprises an upstream cylindrical barrel portion 10 containing a reservoir 11 which is prefilled with helium gas at a pressure of typically 40–80 bar. The upper end of the barrel portion 10 is closed by an end cap 12, having a depending skirt 13. The lower and of the barrel portion 10 is closed by an integral end wall 14 formed with a depending externally screw threaded skirt 15. A plunger 16 has upper and lower cylindrical enlargements 17 and 18, which respectively slide within the skirts 13 and 15. Upward movement of the plunger is limited by abutment of the upper end of the enlargement 17 with a shoulder 19 in the end cap 12. The plunger can be moved downwardly from this position through a stroke equivalent to the gap 20 by downward pressure on a button 21 fixed to the upper end of the plunger 16. This is conveniently performed by the operator holding the barrel 10 in the palm of his hand with his thumb overlying the button. Throughout the stroke, the enlargement 17 remains sealed to the skirt 13 by means of an O ring 22. In the raised position of the plunger, the enlargement 18 is sealed to the skirt 15 by means of an O ring 23 to seal the reservoir 11, but when the plunger is pushed downwardly, the seal 23 exits the lower end of the skirt 15 to provide a quick opening valve which releases gas from the reservoir around the clearance between the smaller diameter portion of the plunger 16 and the skirt 15.

Attached to the bottom of the upper barrel portion 10 is a lower cylindrical barrel portion 24 containing a pressure chamber 25. Attached to the lower end of the barrel portion 24 is a nozzle 26 having an internal passage presenting a short upstream convergent section 27 and a longer downstream divergent section 28. The nozzle 26 has fixed to it a surrounding shroud presenting a cylindrical silencer portion 29 and a divergent spacer portion 30, which extends beyond the end of the nozzle. Interdigitating baffles 31 extend radially inwardly from the cylindrical portion 29 and radially outwardly from the nozzle 26 to provide a tortuous path from within the divergent portion 30 of the shroud to a ring of vents 32. The silencer is constructed and assembled as described in International Publication No. WO 94/24263.

Figure 2:
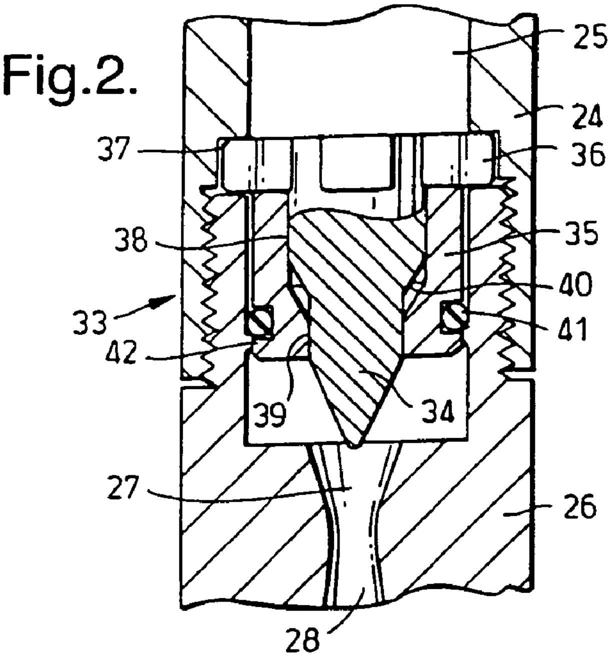
FIGS. 2 and 3 are enlargements of an intermediate portion of the device of FIG. 1, showing the parts before and after firing.
Figure 3:
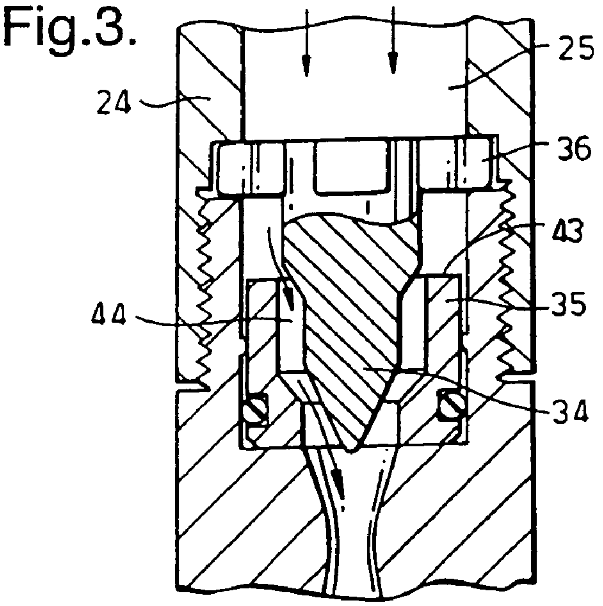

The first example of the syringe of the present invention differs from that of WO 94/24263 in the construction of the replaceable capsule 33, which is depicted in FIG. 1 but more readily understood from FIGS. 2 and 3. The capsule may be a prefilled and sealed unit which is inserted into a chamber defined by the parts 24 and 26 after unscrewing the same and then reattaching them. The capsule comprises two members, a stationary plug or core 34 and a sliding outer housing or sleeve 35. The plug 34 is formed integrally with a ring of radially extending wings 36 which are arranged to be trapped, when the parts 24 and 26 are attached together, between a shoulder 37 on the barrel portion 24 and the upper end of the nozzle 26. The plug 34 is thus held fast. The housing 35 has larger and smaller diameter cylindrical surfaces, 38 and 39, respectively, which surfaces initially confront, as a alight interference fit, complementary cylindrical surfaces of the plug 34. However, the lengths of the cylindrical surfaces are such that, initially, they provide between their transition portions, between the cylindrical surfaces of different diameter, an annular pocket 40 in which the therapeutic agent is contained. An O ring 41, fitted into an annular groove in the sleeve 35, initially abuts an annular projection 42 on the upwardly projecting part of the nozzle 26 and thereby acts to retain the parts 34 and 35 in the initial or closed configuration of FIG. 2.

When the syringe is to be fired, the wider end of the spacer 30 is engaged with a target surface (e.g., skin or mucosal surface) and the button 21 is depressed as previously described to release gas from the reservoir 11 into the pressure chamber 25. The pressure build up is substantially instantaneous to a value at which, acting on the annular upper face 43 of the sleeve 35, it causes the O ring 41 to override the projection 42, allowing the sleeve to move suddenly down to the open or fired configuration of FIG. 3, in which the gas in the pressure chamber 25 can pass (as shown by the arrows in FIG. 3) between the wings 36, and through the passage 44 which is now open as a result of the cylindrical surfaces of the sleeve 35 sliding off of the complementary confronting cylindrical surfaces of the plug 34. The dose of the therapeutic agent which is thus released from the pocket 40 is swept out through the passage 44 and hence into the nozzle 26 where the accelerating gas flow approaches supersonic velocity or greater, with the dose entrained therein, until the flow impinges upon the target surface and delivers the dose into the target surface. The shockwave reflected from the target surface is reflected back through the tortuous path between the baffles 31 to the vents 32 from which the gas is released with minimum report.

Figure 4:
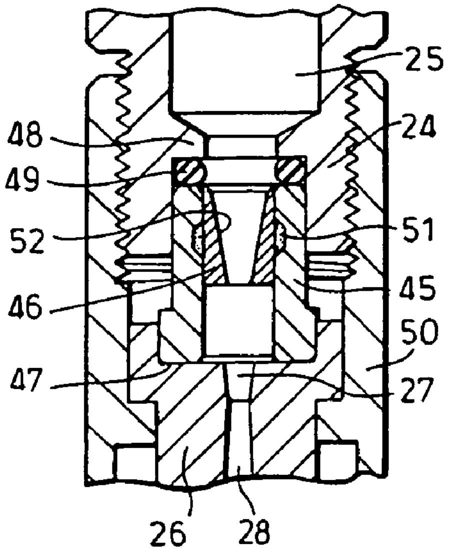
FIGS. 4 and 5 are sections similar to FIGS. 2 and 3, but depict an alternative capsule embodiment.
Figure 5:
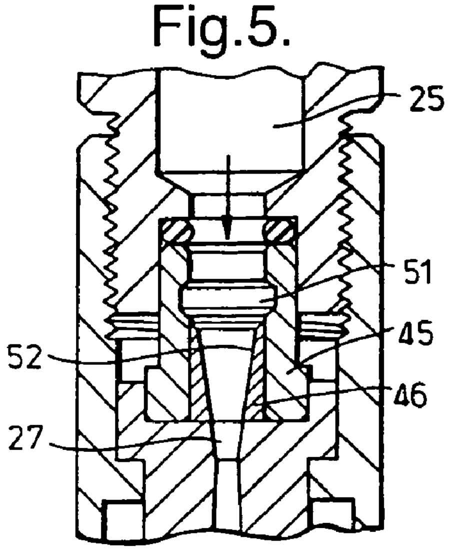

The second example illustrated in FIGS. 4 and 5 has parts which are analogous in function to those of the first example and such corresponding parts are given the same reference numerals as in FIGS. 1–3. In this embodiment, the intermediate portion of the syringe (e.g., the replaceable capsule) is formed from the combination of a stationary outer housing (sleeve) 45 and a slidable internal hollow plug 46, the passage through which is divergently frustaconical. The outer housing 45 is located between a shoulder 47 at the upper end of the nozzle 26, and a shoulder 48 on the lower barrel portion 24, with an interposed O ring 49. The nozzle 26 is not directly attached to the lower barrel portion 24, rather the nozzle is secured by a gland fitting 50 which may form an upper end of the silencer and spacer shroud.

Initially the dose of the therapeutic agent is contained within a pocket 51 that is formed by an annular groove in the inner surface of the outer housing 45, and initially closed by the outer cylindrical surface of the plug 46 which confronts the complementary inner cylindrical surface of the outer housing 45.

When the gas is released from the upper portion of the syringe, pressure builds up almost instantaneously in the pressure chamber 25 and acts upon the internal surface 52 of the plug 46 to cause it to suddenly slide down to the open or fired configuration shown in FIG. 5, in which the pocket 51 is opened to the gas flow passing down from the chamber 25 to the passage 27, 28 through the nozzle 26, flushing out and entraining the dose which is now released. It will be seen that the internal frustoconical surface of the plug 46 complements the upstream convergent portion 27 of the nozzle passage when the device is being fired.

Figure 6:
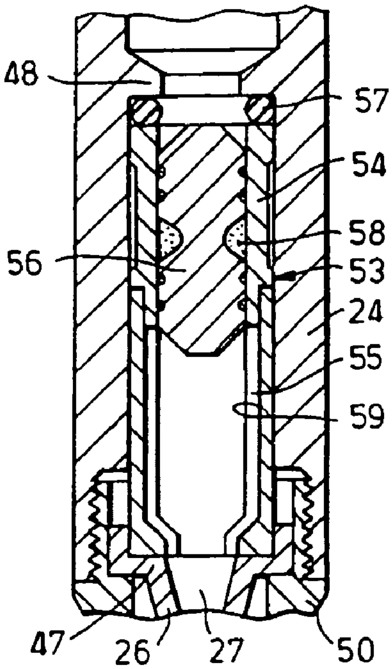
FIGS. 6 and 7 are sections similar to FIGS. 2 and 3, but depict a further alternative capsule embodiment.
Figure 7:
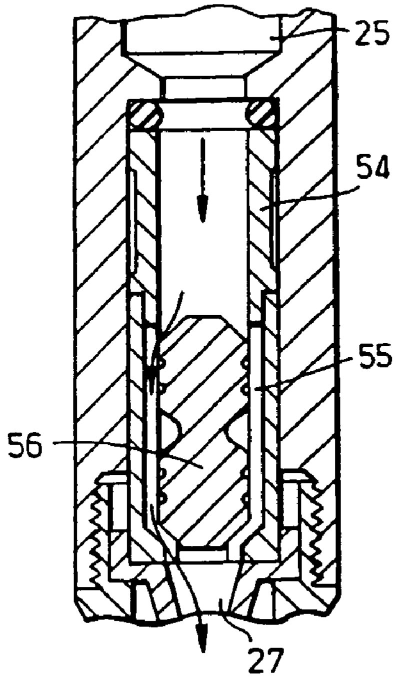
Figure 8:
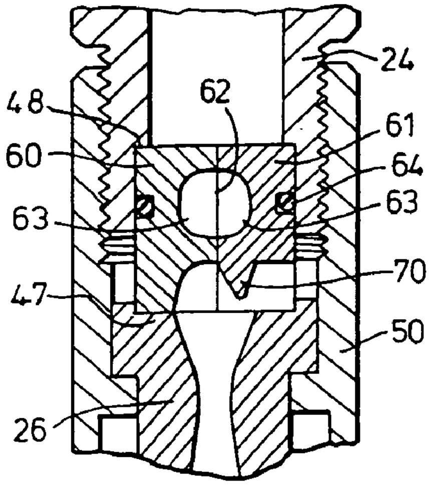
FIGS. 8 and 9 are sections similar to FIGS. 2 and 3, but depict another alternative capsule embodiment.
Figure 9:
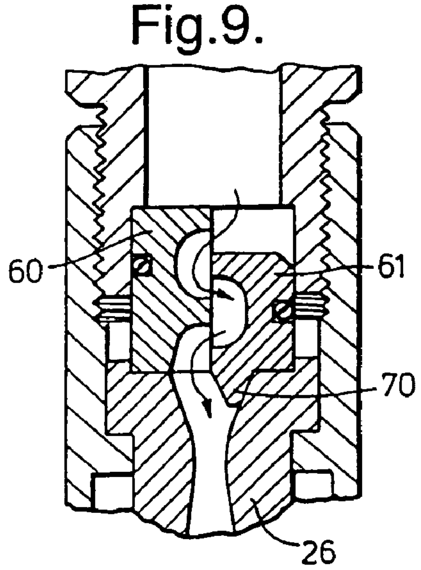

The third example, illustrated in FIGS. 6 and 7, has parts bearing the same reference numerals as parts of analogous function in the first two examples. In this embodiment, the lower barrel portion 24 is bonded to the upper end of the nozzle 26, and a gland fitting 50 attaches into the bottom of the lower barrel portion to locate the replaceable capsule between shoulders 47 and 48. The capsule has an outer stationary housing (sleeve) 53 with an upper generally cylindrical solid upstream portion 54 and an internally axially ribbed downstream portion 55. An internal axially sliding plug (core) 56 is fitted within the housing, and moves relative to the housing within the syringe device.

An O ring 57 seals the capsule to the lower barrel portion 24. The plug 56 has an annular groove which forms a pocket 58 in which the dose of the therapeutic agent is initially contained. The pocket is sealed by upstream and downstream cylindrical external surfaces of the plug which confront the cylindrical internal surface of the upstream portion 54 of the housing 53. The plug 56 has a slight interference fit within the housing 53.

Upon firing, the gas which is released into the pressure chamber 25 acts upon the upper face of the plug 56 and, when the pressure has reached sufficient magnitude, forces the plug downwards so that the pocket 58 is then driven clear of the solid portion 54 of the housing but in alignment with the axially slotted portion 55 of the housing 53. This open or fired arrangement is shown in FIG. 7, and it will be seen that the gas in the chamber 25 is free to pass (as shown by the arrows in FIG. 7) down through the upstream portion 54 of the housing, between the chamfered upper end of the plug 56 and hence through the channels between the ribs 59 of the downstream portion 55 to the nozzle passage 27. The dose of the therapeutic agent is thus swept out and entrained within the gas flow as with the previous examples.

A fourth example of the invention, which is illustrated in FIGS. 8–12, has parts bearing the same reference numerals as parts of analogous function in the first three examples. In this example, similarly to the second example, the capsule is located between shoulders 47 and 48 on the nozzle 26 and lower barrel portion 24, but without the need for an O ring attachment. As can be seen, the capsule is formed from first and second halves of a vertically divided plug. More particularly, the capsule comprises two generally semi-cylindrical portions 60 and 61 which have confronting flat faces abutting each other across an axial plane 62. Both portions 60 and 61 are provided with corresponding recesses 63 such that in the initial or closed configuration, the recesses oppose each other to form a sealed pocket (cavity).

Figure 10:
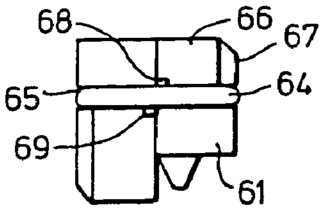
FIGS. 10 and 11 are side elevations of the capsule of FIGS. 8 and 9 before and after firing.
Figure 11:
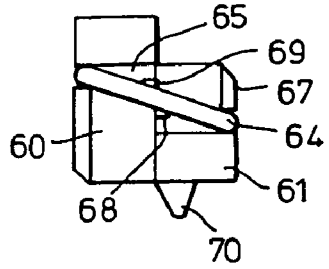
Figure 12:
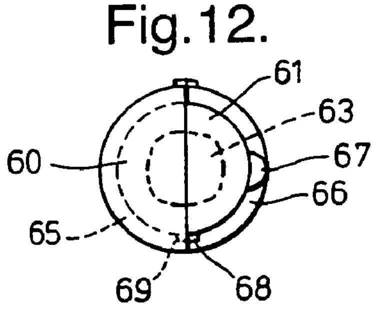
FIG. 12 is a plan view of the capsule of FIGS. 8 and 9, but without a locating 0-ring.

The parts 60 and 61 are initially held in this configuration by an O ring 64 as best seen in FIGS. 10–12. The O ring also serves the function of sealing the capsule to the barrel portion 24. The O ring 64 is located in a semi-annular groove 65 which extends around the periphery of the portion 60, and is disposed within a radially recessed upper part 66 of the portion 61, beneath a projecting nib 67. In this configuration, the O ring 64 lies below a small projection 68 on one or both sides of the portion 61 and above a similar small projection 69 on one or both sides of the portion 60. Thus, the portion 60 is held trapped between the shoulders 47 and 48 when placed within the syringe while the portion 61 is capable of moving, when subjected to sufficient pressure on its upper surface, in a downward direction relative to the portion 60 (i.e., from the initial closed position depicted in FIGS. 6 and 10, to the open or fired position shown in FIGS. 9 and 11).

The relative movement of parts 60 and 61 is initially prevented by a tension provided by the O ring 64 and its abutment with the projections 68 and 69. However, upon firing, when the gas pressure released from the cartridge builds up sufficiently, the force on the upper surface of the portion 61 is sufficient to cause the O ring 64 to override the projection 69 and the projection 68 to underride the O ring, such that the portion 61 moves suddenly downwards to the open position depicted in FIGS. 9 and 11. In this open position, a depending part 70 of the portion 61 mates with the top of the nozzle 26 to provide a passage leading into the nozzle. As will be appreciated from FIG. 9, the previously confronting surfaces of the portions 60 and 61 are moved out of alignment with each other, thereby opening the previously sealed pocket and enabling the gas flow to pass sinuously through the capsule (as shown by the arrows) and into the passageway through the nozzle 26, flushing out and entraining the dose of the therapeutic agent within the gas flow.

Figure 13:
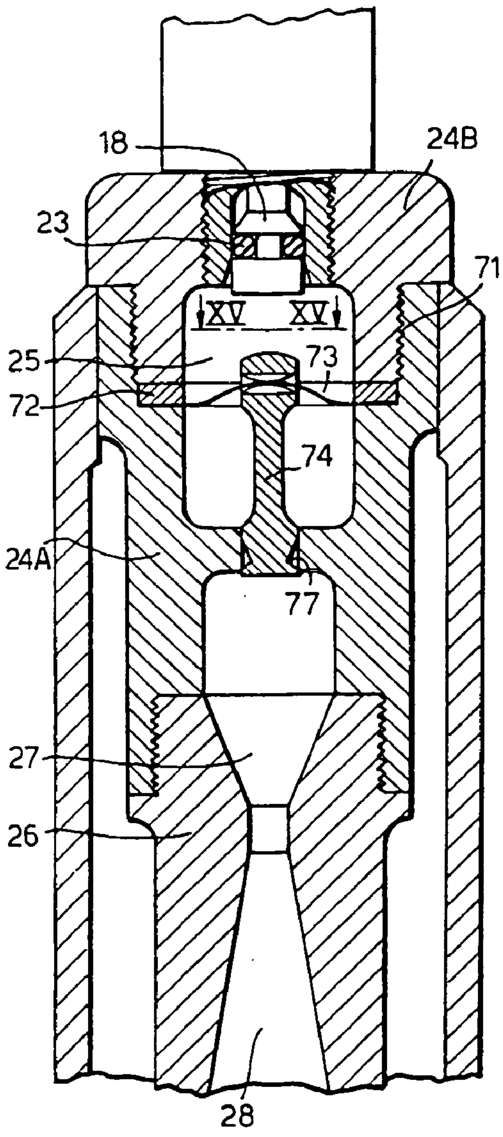
FIGS. 13 and 14 are sections similar to FIGS. 2 and 3, but depict yet a further capsule embodiment.
Figure 14:
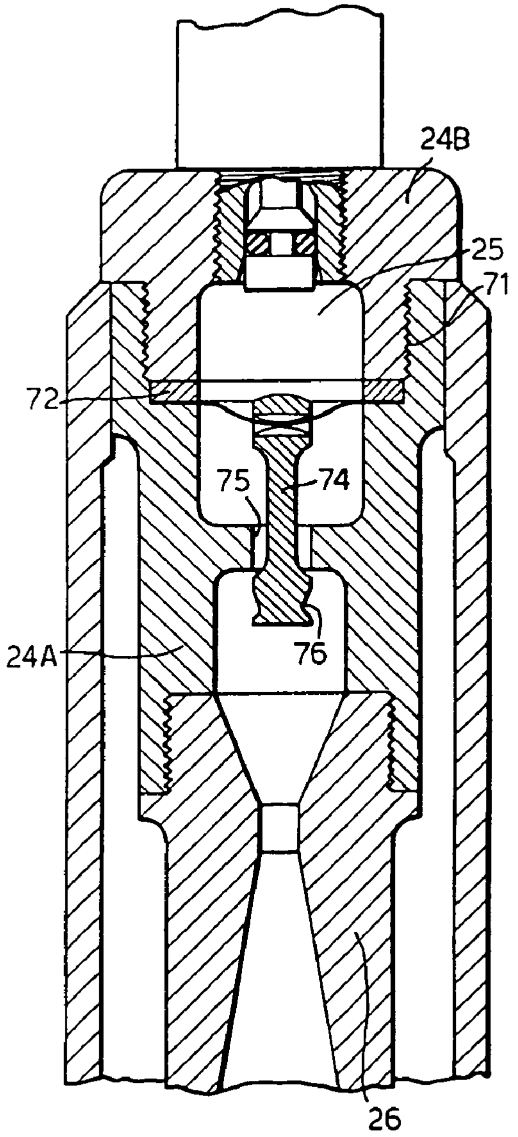
Figure 15:
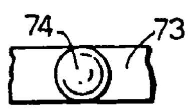
FIG. 15 is a section through line XV—XV in FIG. 13.

The fifth example, illustrated in FIGS. 13 and 14, has parts bearing the same reference numerals as corresponding parts in the first four examples. In this case, the lower barrel portion comprises two parts 24A and 24B which are connected together by a screw thread 71 so as to retain a ring 72. A bar 73, which is initially biased in an upwardly deflected (buckelled) position as shown in FIG. 13, is held at both ends by (e.g., fixed across) the ring 72. The bar 73 supports an upper end of a plunger 74 having a lower end which is disposed within and closes off an opening 75 in the lower barrel portion 24A, which portion forms part of a tubular housing and cooperates with the plunger. More particularly, the plunger 74 has an annular recess 76 at its lower end which cooperates with the wall of the opening 75 to define a pocket 77 which initially contains the dose of the therapeutic agent.

The bar 73 can be made from any suitable material which allows for such tensioned movement. For example, the bar can be formed from a laminate of polymeric strips which are bonded (e.g., heat sealed) at their ends to form a structure similar to a leaf spring.

Upon firing, the gas pressure within the pressure chamber 25 acts upon the upper surface of the upwardly deflected bar 73 and forces it to deflect rapidly through a dead-center position to a position in which the direction of buckelling is effectively reversed as shown in FIG. 14. This causes the plunger to quickly travel down through the opening 75, thereby both providing a passage through the syringe and opening the pocket 77 to allow the dose to be entrained within the passing gas flow.

Figure 16:
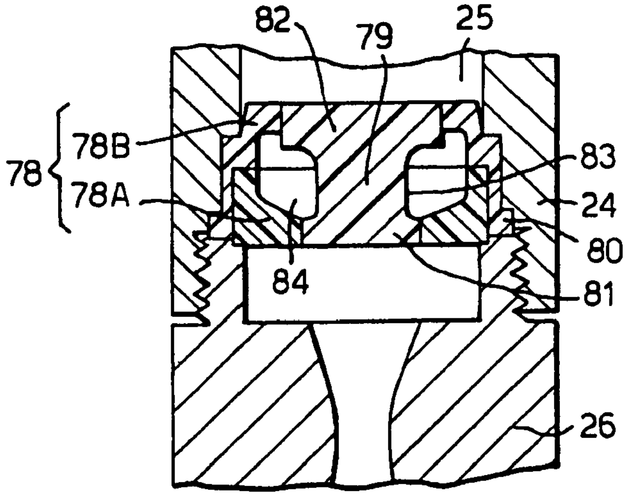
FIGS. 16 and 17 are sections similar to FIGS. 2 and 3, but depict another capsule embodiment.
Figure 17:
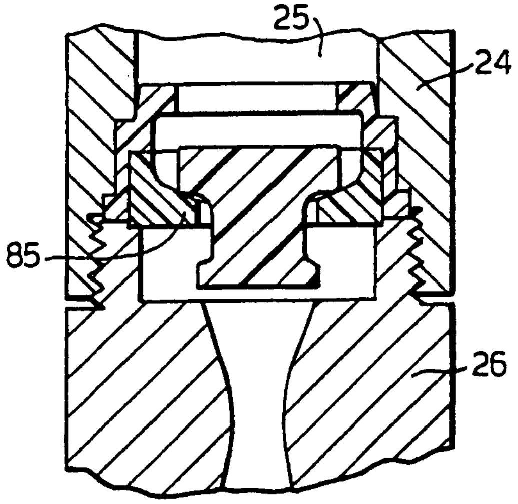

The sixth example, illustrated in FIGS. 16 and 17, has parts bearing the same reference numerals as parts of analogous function in the first five examples. In this example, the replaceable capsule is formed from the combination of three pieces, that is, first and second capsule housing parts, 78A and 78B, which are assembled to provide a capsule housing 78, and a plug 79 which is retained within the capsule housing. The capsule housing 78 has a radially outwardly projecting flange 80 which is sandwiched between the lower barrel portion 24 and nozzle 26. The plug 79 has a first head 81 at its lower end, and a second head 82 at its upper end. The second head 82 has a larger diameter than that of the first head 81, while the diameter of first head 81 is larger than the diameter of a mid-portion 83 of the plug which is interposed between the first and second heads. The outer surface of this mid-portion cooperates with the capsule housing 78 in order to define a pocket 84 for containing the dose of the therapeutic agent. Initially, the capsule is sealed by virtue of an interference fit between the first and second heads 81 and 82, and the capsule housing 78.

The plug 79 and capsule housing 78 can be formed from any suitably resilient materials, for example, high density polymers and/or metals. Preferably, the first and second portions of the capsule housing are formed from a high density polyethylene (HDPE), and the plug is formed from either HDPE or a metal such as brass or stainless steel, wherein the plug material is sufficiently resistant to deformation during use.

When the syringe is fired, application of high pressure gas in the chamber 25 acts upon the upper surface of the plug 79 forcing it to travel in a downward direction within the syringe to the open or fired position depicted in FIG. 17. In this open position, the lower surface of the second head 82 abuts against an upper surface of a lip 85 extending around the lower periphery of the capsule housing thereby preventing further movement of the plunger. Radially extending vanes (not shown) on-the underside of the second head 82 and/or on the upper surface of the lip 85 provide a passage for the gas flow into the nozzle 26.

Instead of an interference fit between facing surfaces of the plug 79 and the capsule housing 78, an arrangement having an O ring and override projection similar to that shown in FIGS. 2 and 3 can be incorporated in order to provide resistance against initial movement of the plug within housing.

As an alternative to the second head 82 being caught by the lip 85, travel of the plug can be stopped by an abutment arranged within the device at a position which is downstream of the plunger 79 (when in its initial closed position). The abutment can be provided, for example, by a rim around the upstream end of the convergent section 27 having a diameter less than the diameter of the downstream end of the plug, or by a bar fixed across the upstream end of the convergent section. Alternatively, the first capsule housing 78A can be extended toward the upstream end of the convergent section, and a bar or some other depending feature can be provided within the capsule housing which serves to stop travel of the plug during firing.

Figure 18:
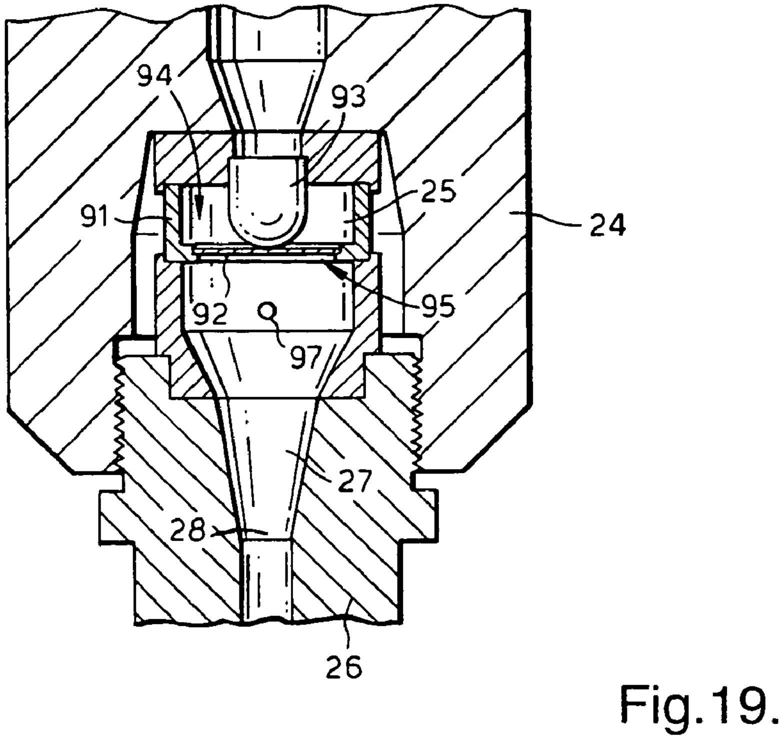
FIGS. 18 and 19 are sections similar to FIGS. 2 and 3, but depict a still further capsule embodiment.
Figure 19:
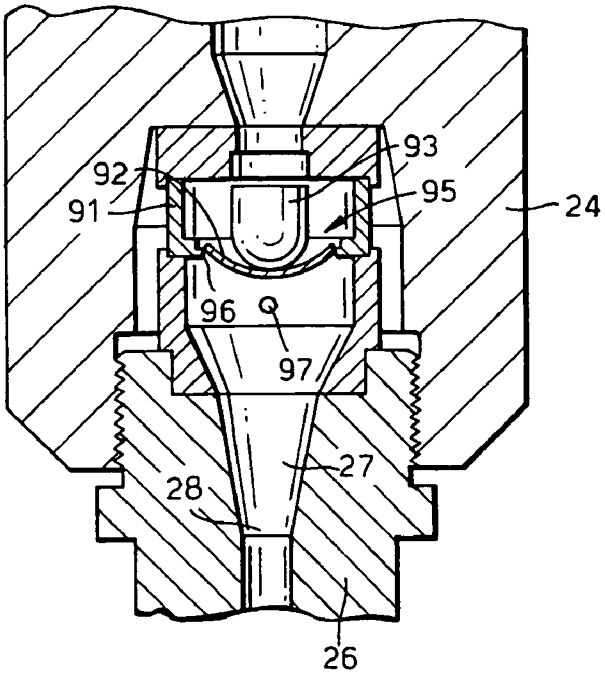

The seventh example, illustrated in FIGS. 18 and 19, has parts bearing the same reference numerals as parts of analogous function in the first six examples. In this example, the replaceable capsule is formed from the combination of a tubular housing 91 which forms or is disposed within the pressure chamber 25, a thin flexible disk 92, and a plug 93. The housing 91 has an upstream opening 94 and a downstream opening 95, wherein the disk 92 closes off the downstream opening, and the plug 93 closes off the upstream opening. In the particular configuration depicted in FIGS. 18 and 19, the plug 93 closes off the upstream opening the pressure chamber 25, and the upstream opening 94 of the housing 91 is abutted against the upper portion of the pressure chamber to define a sealed chamber. In the initial closed position of the capsule before firing (as shown in FIG. 18), the inner surface of the housing 91, the outer surface of the plug 93, and the upstream surface of the disk 92 serve to establish the closed pocket in which the dose of the therapeutic agent is contained.

In use, a gas pressure is released through the upstream portion of the syringe which builds up above the plug 93 until it reaches sufficient magnitude to dislodge the plug from its seat in the upstream opening of the housing, and travel in a downward direction within the syringe. Movement of the plug 93 causes the disk to flex downwardly through the downstream opening 95 of the housing 91 (as shown in FIG. 19), allowing the plug to pass out of the upstream opening of the housing whereupon pressure builds up within the chamber 25. When the pressure has reached sufficient magnitude, the disk 92 bows enough to be dislodged from its seated position on a lip 96 which is provided at the downstream opening of the housing 91, and pass into a downstream portion of the syringe. This provides a passage through the capsule and into the nozzle 26, and the gas may then flow through the intermediate portion of the syringe, flushing out and entraining the dose of the therapeutic agent for delivery to a target surface.

The disk 92 and the plug 93 may be molded as a single piece, the plug may simply rest upon the upper surface of the disk, or the plug may be attached to the upper surface of the disk. Furthermore, an optional stop, which can be in the form of a depending tab 97 arranged on the inner surface of the syringe, can be provided to prevent the disk and plug from traveling into the upstream opening of the nozzle 26.

Accordingly, novel syringe devices and capsules for use therein are disclosed. Although preferred embodiments of the subject invention have been described in some detail, it is understood that obvious variations can be made without departing from the spirit and the scope of the invention as defined by the appended claims.

We claim:

1. A capsule comprising:

a first member and a second member, wherein said capsule is adapted for containing a dose of particles to be delivered within a pressurized fluid flow, wherein said first and second members are coupled together to provide a closed pocket within the members for containing the dose, wherein one of said first and second members is configured to slide relative to the other member when an external portion of said capsule is contacted with the pressurized fluid flow, and wherein said first and second members are constructed and arranged such that upon said relative movement a passage is formed through said capsule and said pocket is opened to expose the dose of particles for entrainment in the pressurized fluid flowing through said passage.

2. The capsule of claim 1, wherein the first and second members are respectively first and second halves of a vertically divided plug.

3. The capsule of claim 2, wherein the first and second halves of the plug contact each other at opposing faces thereof, and the closed pocket is provided by corresponding cavities disposed within said opposing faces.

4. The capsule of claim 1, wherein the first and second members are coupled together to form the closed pocket by a resilient coupling means.

5. The capsule of claim 1, wherein said closed pocket is prefilled with the dose of the particles and said first and second members are sealably coupled together.

6. The capsule of claim 1, wherein the particles comprise a therapeutic agent.

7. A capsule adapted for containing a dose of particles to be delivered within a pressurized fluid flow, said capsule comprising:

a first member and a second member, wherein said first and second members are coupled together to provide a closed pocket within the members for containing the dose, and one of said first and second members is moveable relative to the other member when an external portion of said capsule is contacted with a pressurized fluid flow, said first and second members being constructed and arranged such that upon said relative movement a passage is formed through said capsule and said pocket is opened to expose the dose for entrainment in fluid flowing through said passage, and wherein the second member is a housing and the first member is a plug which is inserted into said housing.

8. The capsule of claim 7, wherein the plug is moveable within the housing when said capsule is contacted with a pressurized fluid flow.

9. The capsule of claim 7, wherein the housing is moveable from around the plug when said capsule is contacted with a pressurized fluid flow.

10. The capsule of claim 7, wherein the particles comprise a therapeutic agent.

11. A capsule adapted for containing a dose of particles to be delivered within a pressurized fluid flow, said capsule comprising:

a first member and a second member, wherein said first and second members are coupled together to provide a closed pocket within the members for containing the dose, and one of said first and second members is moveable relative to the other member when a portion of said capsule is contacted with a pressurized fluid flow, said first and second members being constructed and arranged such that upon said relative movement a passage is formed through said capsule and said pocket is opened to expose the dose for entrainment in fluid flowing through said passage, wherein the second member is a housing and the first member is a plug which is inserted into said housing, and wherein the plug and the housing contact each other at upper and lower opposing faces thereof, and the closed pocket is provided by an intermediate space established between said upper and lower opposing faces where said plug and housing do not contact each other.

12. The capsule of claim 11, wherein the particles comprise a therapeutic agent.

13. A capsule adapted for containing a dose of particles to be delivered within a pressurized fluid flow, said capsule comprising:

a first member and a second member, wherein said first and second members are coupled together to provide a closed pocket within the members for containing the dose, and one of said first and second members is moveable relative to the other member when a portion of said capsule is contacted with a pressurized fluid flow, said first and second members being constructed and arranged such that upon said relative movement a passage is formed through said capsule and said pocket is opened to expose the dose for entrainment in fluid flowing through said passage, wherein the second member is a housing and the first member is a plug which is inserted into said housing, and wherein the plug and the housing contact each other at upper and lower opposing faces thereof, and further wherein the closed pocket is provided by a cavity or recess formed in the plug and/or housing, and said cavity or recess is positioned between said upper and lower opposing faces.

14. The capsule of claim 13, wherein the cavity or recess is annular.

15. The capsule of claim 13, wherein the cavity or recess is formed in the plug.

16. The capsule of claim 15, wherein the cavity or recess is also formed in the housing.

17. The capsule of claim 13, wherein the particles comprise a therapeutic agent.

18. A capsule comprising:

a first member and a second member, wherein said capsule is adapted for containing a dose of a therapeutic agent to be delivered within a pressurized fluid flow, wherein said first and second members are coupled together to provide a closed pocket within the members for containing the dose, wherein one of said first and second members is configured to slide relative to the other member when an external portion of said capsule is contacted with the pressurized fluid flow, and wherein said first and second members are constructed and arranged such that upon said relative movement a passage is formed through said capsule and said pocket is opened to expose the dose of the therapeutic agent for entrainment in the pressurized fluid flowing through said passage.

19. The capsule of claim 18, wherein the fluid is a compressible gas.

20. The capsule of claim 18, wherein the dose of the therapeutic agent is in particulate form.

21. A syringe for delivering a dose of particles within a pressurized fluid flow, said syringe comprising:

(a) an upstream portion which is interfaced with a source of fluid under pressure;

(b) a downstream nozzle portion;

(c) an intermediate portion arranged between the upstream and downstream portions, wherein said intermediate portion comprises first and second members which are coupled together to provide a closed pocket within the members for containing the dose of the particles, and further wherein one of said first and second members is configured to slide relative to the other member; and (d) an actuator mechanism for initiating a flow of fluid from the source of fluid to the intermediate portion whereby pressure exerted by the fluid causes one of said first and second members to move relative to the other member, said first and second members being constructed and arranged such that upon said relative movement a passage is formed through said intermediate portion and said pocket is opened to expose the dose for entrainment in the fluid flowing through said passage and into the downstream nozzle portion.

22. The syringe of claim 21, wherein the first member of the intermediate portion comprises a tubular housing having an upstream opening and a downstream opening, the second member of the intermediate portion comprises a plunger having a lower end which is disposed within and closes off said downstream opening of said housing, and the closed pocket is provided by a space established between the lower end of the plunger and the inner surface of the downstream opening.

23. The syringe of claim 22, wherein the closed pocket is further provided by a cavity disposed within the lower end of the plunger.

24. The syringe of claim 22, wherein an upper end of the plunger extends toward the upstream portion of the syringe and is supported by a bar which is supported at both ends by the intermediate portion of the syringe and is initially deflected towards the upstream portion of the syringe.

25. The syringe of claim 24, wherein pressure exerted by the fluid causes the bar to travel through a dead-center position and deflect towards the downstream portion of the syringe, thereby causing the lower end of the plunger to dislodge from said downstream opening and move in a downstream direction relative to the housing to provide a passage through said intermediate portion of the syringe.

26. The syringe of claim 21, wherein the fluid is a compressible gas.

27. The syringe of claim 21 further comprising means for providing resistance against initial movement of said first or second member relative to the other member.

28. The syringe of claim 21, wherein the closed pocket is prefilled with the dose of the particles and said first and second members are sealably coupled together.

29. The syringe of claim 28 further comprising means for providing resistance against initial movement of said first or second member relative to the other member.

30. The syringe of claim 21, wherein the first member of the intermediate portion comprises a tubular housing having an inner surface, an upstream opening and a downstream opening, and the second member of the intermediate portion comprises a disk having a centrally disposed plug attached thereto, wherein said disk closes off the downstream opening of said housing and said plug extends toward the upstream portion of the syringe and closes off the upstream opening of said housing, and further wherein the closed pocket is provided by an annular space established between the disk, the outer surface of the plug, and the inner surface of the housing.

31. The syringe of claim 30, wherein pressure exerted by the fluid causes the plug to dislodge from the upstream opening and move in a downstream direction relative to the housing, thereby exerting sufficient pressure upon the disk to deform and cause said disk to pass through the downstream opening and create a passage through the intermediate portion of the syringe.

32. The syringe of claim 21, wherein the particles comprise a therapeutic agent.

33. A syringe for delivering a dose of particles within a pressurized fluid flow, said syringe comprising:

(a) an upstream portion which is interfaced with a source of fluid under pressure;

(b) a downstream nozzle portion;

(c) an intermediate portion arranged between the upstream and downstream portions, wherein said intermediate portion comprises first and second members which are coupled together to provide a closed pocket for containing the dose of the particles, and further wherein one of said first and second members is configured to slide relative to the other member; and (d) an actuator mechanism for initiating a flow of fluid from the source of fluid to the intermediate portion whereby pressure exerted by the fluid causes one of said first and second members to move relative to the other member, said first and second members being constructed and arranged such that upon said relative movement a passage is formed through said intermediate portion and said pocket is opened to expose the dose for entrainment in the fluid flowing through said passage and into the downstream nozzle portion, wherein the closed pocket is prefilled with the dose of the particles and said first and second members are sealably coupled together, and wherein the fluid is a compressible gas.

34. The syringe of claim 33, wherein the particles comprise a therapeutic agent.

* * * * *